US010369253B2

(12) United States Patent
Bhaduri et al.

(10) Patent No.: US 10,369,253 B2
(45) Date of Patent: Aug. 6, 2019

(54) METHOD FOR MODIFYING SURFACES FOR BETTER OSSEOINTEGRATION

(71) Applicant: The University of Toledo, Toledo, OH (US)

(72) Inventors: Sarit B. Bhaduri, Holland, OH (US); Vijay K. Goel, Holland, OH (US); Huan Zhou, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 14/355,051

(22) PCT Filed: Oct. 31, 2012

(86) PCT No.: PCT/US2012/062854
§ 371 (c)(1),
(2) Date: Apr. 29, 2014

(87) PCT Pub. No.: WO2013/067049
PCT Pub. Date: May 10, 2013

(65) Prior Publication Data
US 2014/0308334 A1    Oct. 16, 2014

Related U.S. Application Data

(60) Provisional application No. 61/553,611, filed on Oct. 31, 2011.

(51) Int. Cl.
*A61L 27/32*    (2006.01)
*A61L 27/54*    (2006.01)
(Continued)

(52) U.S. Cl.
CPC ............... *A61L 27/32* (2013.01); *A61L 27/00* (2013.01); *A61L 27/12* (2013.01); *A61L 27/54* (2013.01);
(Continued)

(58) Field of Classification Search
None
See application file for complete search history.

(56) References Cited

U.S. PATENT DOCUMENTS 5,759,376 A    6/1998    Teller et al.
6,143,948 A *   11/2000    Leitao et al. ................ 424/422
(Continued)

FOREIGN PATENT DOCUMENTS

| CN | 101491698 A | 7/2009 |
| CN | 101920947 A | 12/2010 |
| EP | 2042200 A1 | 4/2009 |

OTHER PUBLICATIONS

Pradas et al. (Surface modification of P(EMA-co-HEA)/SiO2 nanohybrids for faster hydroxyapatite deposition in simulated body fluid?, Colloids and Surfaces B: Biointerfaces, 2009, vol. 70, pp. 218-225).*

(Continued)

*Primary Examiner* — Bethany P Barham
*Assistant Examiner* — Dominic Lazaro
(74) *Attorney, Agent, or Firm* — MacMillan, Sobanski & Todd, LLC

(57) ABSTRACT

In one aspect, there is provided a method for preparing a biocompatible coated substrate. The method generally includes: depositing nucleation amorphous calcium phosphate sites on at least a portion of an outer surface of a substrate by: exposing at least the portion of the outer surface to a mixture having a favorable Ca/P molar ratio, and irradiating with microwave energy; and, stabilizing the deposited nucleation amorphous calcium phosphate sites on the portion of the outer surface. In another aspect, there is provided herein a method for preparing a biocompatible coated substrate.

13 Claims, 8 Drawing Sheets
(8 of 8 Drawing Sheet(s) Filed in Color)

(51) Int. Cl.
- A61L 27/00 (2006.01)
- A61L 27/12 (2006.01)
- A61L 29/10 (2006.01)
- A61L 31/08 (2006.01)

(52) U.S. Cl.
CPC ........... *A61L 29/106* (2013.01); *A61L 31/086* (2013.01); *A61L 2400/18* (2013.01); *A61L 2430/02* (2013.01)

(56) References Cited

U.S. PATENT DOCUMENTS

| | | | |
|---|---|---|---|
| 6,569,489 B1* | 5/2003 | Li | 427/2.26 |
| 2005/0226939 A1* | 10/2005 | Ramalingam | C01B 25/32 424/602 |
| 2005/0268819 A1 | 12/2005 | Lin et al. | |
| 2009/0022811 A1 | 1/2009 | LeGeros et al. | |
| 2009/0068245 A1 | 3/2009 | Noble et al. | |
| 2010/0016985 A1* | 1/2010 | Rabiei | A61K 6/08 623/23.6 |
| 2010/0129416 A1* | 5/2010 | Murphy | A61L 27/446 424/423 |
| 2011/0046404 A1 | 2/2011 | Sharma et al. | |
| 2012/0192481 A1 | 8/2012 | O'Connor | |

OTHER PUBLICATIONS

Rao et al. (Rapid microwave assisted synthesis of hydroxyapatite, Bull. Mater. Sci., 1996, pp. 1163-1165.*

Tas et al. (Rapid coating of ti6al4v at room temperature with a calcium phosphate solution similar to 10x simulated body fluid, J. Mater. Res. 2004, vol. 19, pp. 2742-2749.*

Kumar et al., Rapid synthesis of calcium deficient hydroxyapatite nanoparticles by microwave irradiation, Trenda Biomater. Artif. Organs. 2005, vol. 18, p. 110-113.*

Colak et al., Synthesis, characterization and osteoblastic activity of polycaprolactone nanofibers coated with biomimetic calcium phosphate, Acta Biomaterialia, 2009, vol. 5, p. 3098-3111.*

Bhaduri et al., rapid coating of AZ3 magnesium alloy with calcium deficient hydroxyapatite using microwave energy, Material Science and Engineering C, 2015, vol. 49, p. 364, right column, 2nd para.; p. 364-372.*

Wang et al., Functional Coating or Films for Hard-tissue Application, Materials, 2010, vol. 3, 3994-4050.*

Lidstrom et al. (microwave assisted organic synthesis—a review, Tetrahedron, 2001, p. 9226-9228, 9231.*

Loupy et al., A tentative rationalization of microwave effects in organic synthesis according to the reaction medium, and mechanistic considerations, Tetrahedron, 2001, p. 9200-9202.*

Wadsworth Publishing Company, second law of thermodynamics, slide 1-8, 14, 19-22, 1997.*

Pino et al. (Nucleation and growth of apatite on NaOH-treated PEEK, HDPE and UHMWPE for artificial cornea materials, Acta Biomaterialia, 2008, p. 1827-1938).*

European Partial Search Report, Application No. 12846122.5 dated May 4, 2015.

Bakar, et al., Mechanical Properties of Injection Molded Hydroxyapatite-Polyetheretherketone Biocomposites, Composites Science and Technology, 2003, vol. 63, pp. 421-425.

Borum, et al., Surface Modification of Hydroxyapatite. Part II. Silica, Biomaterials 2003, vol. 24, pp. 3681-3688.

Converse, et al., Processing and Tensile Properties of Hydroxyapatite-Whisker-Reinforced Polyetheretherketone, Biomaterials, 2007, vol. 28, pp. 927-935.

Dorozhkin, Bioceramics of Calcium Orthophosphates, Biomaterials, 2010, vol. 31, pp. 1465-1485.

Kokubo, T., Surface Chemistry of Bioactive Glass-Ceramics, Journal of Non-Crystalline Solids, 1990, vol. 120, pp. 138-151.

Marques, et al., Simulated Biological Fluids with Possible Application in Dissolution Testing, Dissolution Technologies, 2011, pp. 15-28.

PCT International Search Report and The Written Opinion, Application No. PCT/US2012/062854, filed Oct. 31, 2012, dated Jan. 25, 2013.

Pino, et al., Nucleation and Growth of Apatite on NaOH-treated PEEK, HDPE and UHMWPE for Artificial Cornea Materials, Acta Biomaterialia, 2008, vol. 4, pp. 1827-1836.

Sanpo, et al., Antibacterial Property of Cold-Sprayed HA-Ag/PEEK Coating, Journal of Thermal Spray Technology, 2009, vol. 18(1), pp. 10-15.

Tan, et al., Scaffold Development using Selective Laser Sintering of Polyetheretherketone-Hydroxyapatite Biocomposite Blends, Biomaterials, 2003, vol. 24, pp. 3115-3123.

European Search Report, Application No. 12846122.5, dated Jan. 29, 2018.

* cited by examiner

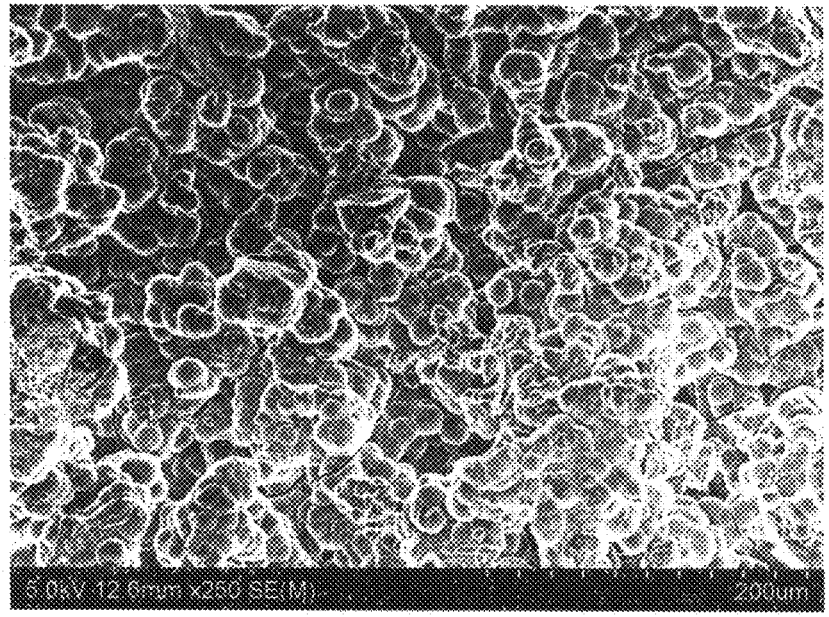
Prior Art - Figure 1A
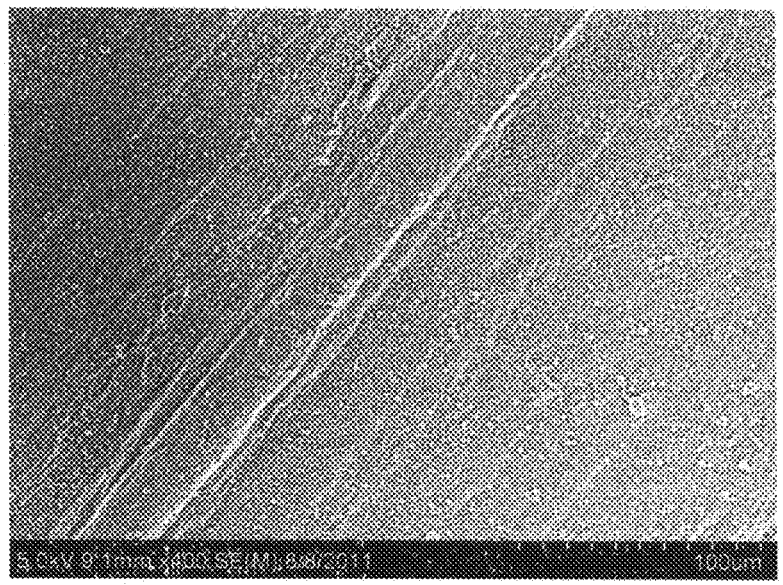
Figure 1B

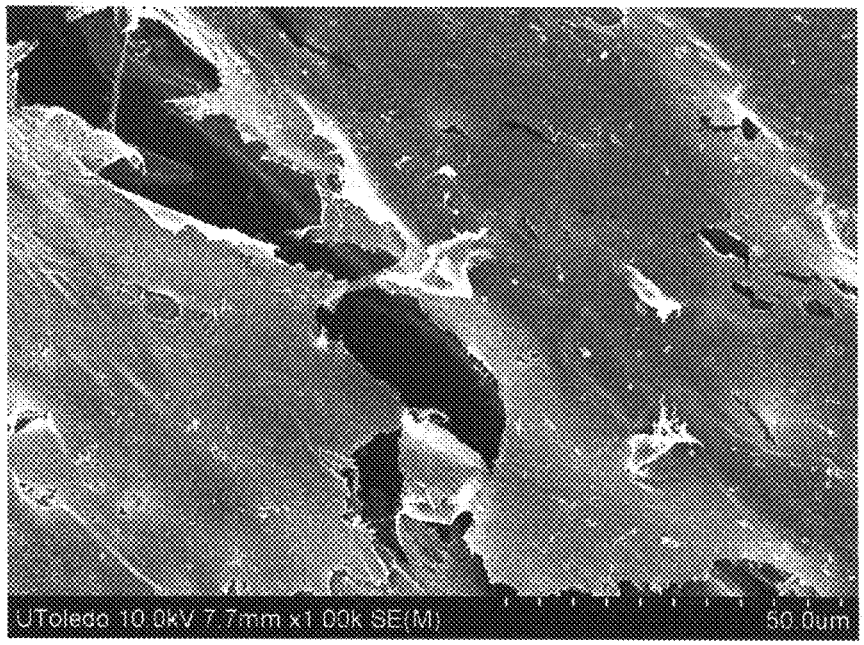
Prior Art - Figure 7
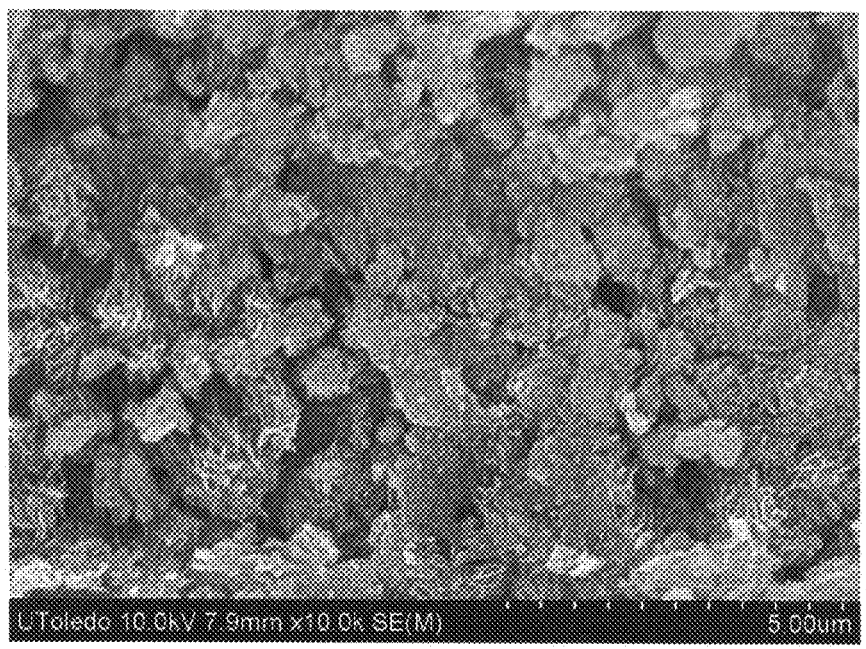
Figure 8A

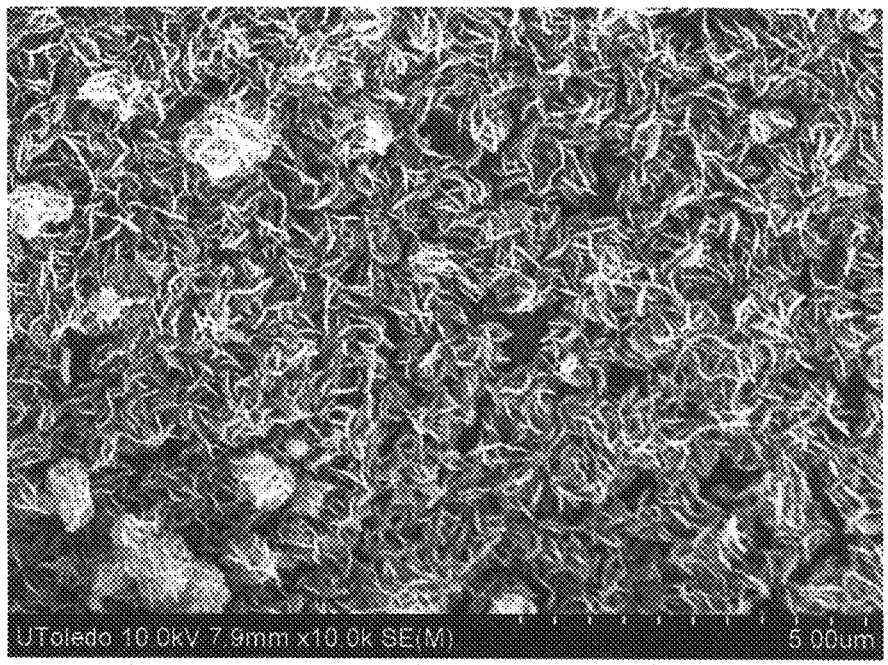
Figure 8B
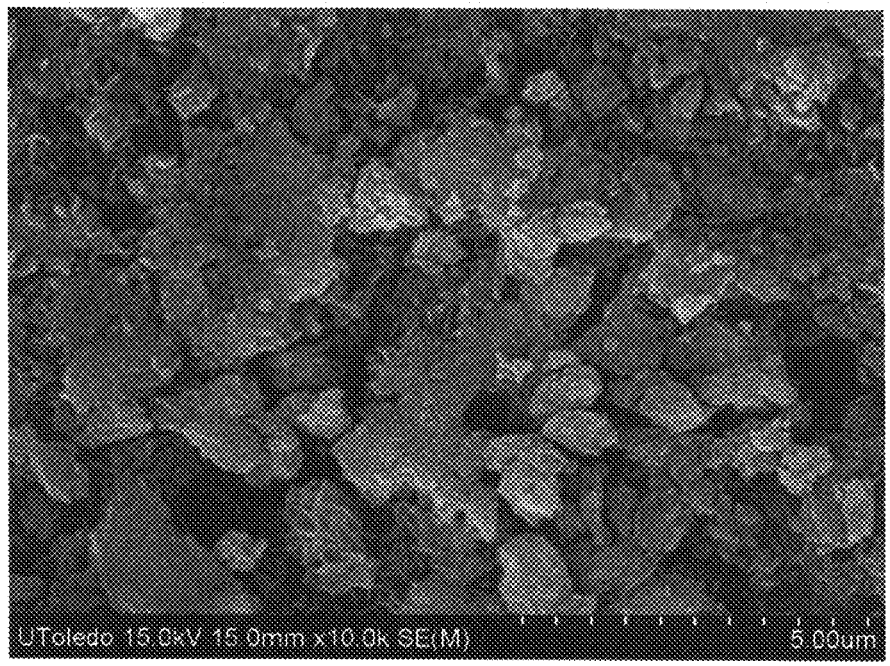
Prior Art - Figure 8C

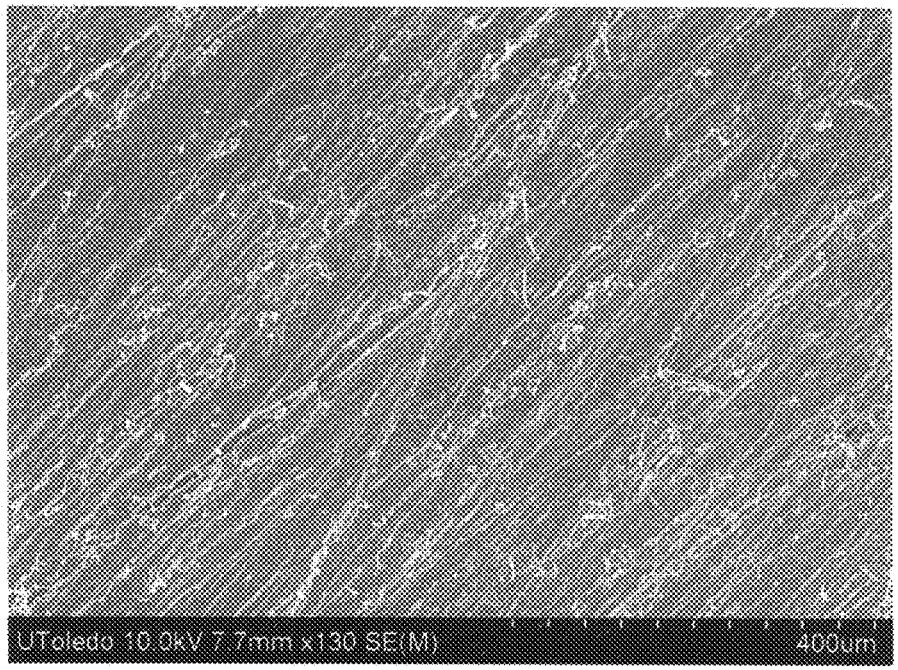
Prior Art - Figure 11A
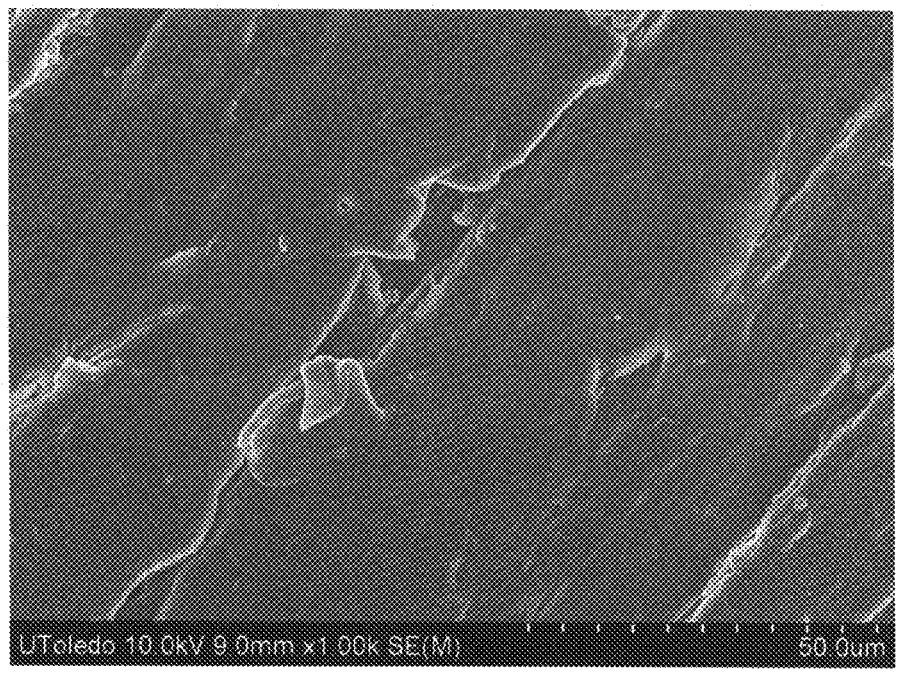
Prior Art - Figure 11B

METHOD FOR MODIFYING SURFACES FOR BETTER OSSEOINTEGRATION

CROSS-REFERENCE TO RELATED APPLICATIONS

This is a national stage application filed under 37 C.F.R. § 1.371 of international application PCT/US2012/062854, filed under the authority of the Patent Cooperation Treaty on Oct. 31, 2012, published; which claims priority to U.S. Provisional Application Ser. No. 61/553,611 filed under 35 U.S.C. § 111(b) on Oct. 31, 2011. The entire disclosures of all priority applications are incorporated herein by reference.

STATEMENT REGARDING FEDERALLY SPONSORED RESEARCH

The invention was made with U.S. Government support under Grant No. 0700306 awarded by the National Science Foundation. The United States Government has certain rights in the invention.

TECHNICAL FIELD AND INDUSTRIAL APPLICABILITY OF THE INVENTION

The present invention relates to methods for preparing biocompatible coated substrates and devices made thereby.

BACKGROUND OF THE INVENTION

The treatment of injuries or diseases of hard tissues often requires surgical action. In general, bone fractures are usually treated with wires, nails, screws, and plates; joints are replaced by artificial endoprostheses; and, lost teeth are replaced by implants in the jaw. There are mainly three types of materials used for manufacturing dental/orthopedic implants: metals, polymers and ceramics.

Metallic implants are typically made of elemental metals such as titanium, tantalum, niobium, zirconium and related alloys, certain types of stainless steel, cobalt-chrome alloys. All show good mechanical strength and biocompatibility, but lack in their ability to form direct bonds to new formed bone tissue in the body. As a result, these metals rub against the bones into which they have been implanted, creating wear and tear that shortens implant lifetimes.

Polymeric implants can generally be divided into two categories: one is a biocompatible polymer that has biochemical and biomechanical properties suitable for load bearing orthopedic implants, such as polyetheretherketone (PEEK), ultra high molecular weight polyethylene (UHMWPE), polymethyl methacrylate (PMMA), and the like. These thermoplastic materials, however, have the same problems as biocompatible metallic materials. The other polymeric category is bioactive polymers that are generally used as a temporary scaffold for tissue engineering applications. Examples of such bioactive polymers include polylactic acid (PLA), its co-polymer with glycolic acid (PLGA), polycaprolactone (PCL), polyhydroxyalkanoates (PHA) such as poly-3-hydroxybutyrate (P3HB), and the like. Due to their degradation in vivo, they have limited load carrying capability.

Ceramic implants such as bioglass and some calcium phosphates (CaPs), on the other hand, have an ability to form bonds with hard tissues such as bone tissue. There are several compounds in the calcium phosphate system with different degrees of biocompatibilities. The ceramic implants can be fabricated into 3D scaffolds for tissue engineering applications, but are limited in their application due to their brittleness. To overcome the brittle behavior of ceramics, toughened ceramics such as zirconia and related materials can be used. Still, such toughened ceramic implants are only biocompatible, not bioactive.

One particular CaP material is a hydroxyapatite (HA) compound that is similar to bone minerals, and has received approval by the FDA for many applications. Other CaP materials include, for example, tricalcium phosphate (TCP) and the like.

In certain cases, the CaP materials can be combined with metallic, polymer, or ceramic implants and used as coatings. However, there are still concerns with such coated CaP implants that are related to the chemical composition itself, and its crystallinity, biodegradability and useful thicknesses. These are of particular concern in the manufacturing since, in order to achieve the desirable crystallinity and biodegradability, the relevant manufacturing process may take such long times that is not commercially viable.

Another concern is the ability to manufacture implants that are suitable for extended use in a human body; for example, a CaP coating thickness on an implant of about 100 μm or greater can introduce fatigue under tensile loading. Moreover, it has been found that the residual stress increases with thickness, and its energy release may promote interfacial debonding.

In a past biomimetic coating technique, $Ca^{2+}$ and $PO_4^{3-}/HPO_4^{2-}$ in solution randomly form amorphous calcium phosphate (ACP) precursors that are capable of binding to active medical device surface as nucleation sites. However, the ACP precursors are very unstable and subsequently undergo rapid phase transformation into other calcium phosphate (CaP) materials, such as octacalcium phosphate (OCP) and hydroxyapatite (HA) with adsorption of extra $Ca_{2+}$ and $PO_4^{3-}/HPO_4^{2-}$ ions from solution. Another important and serious drawback of this biomimetic coating technique that the process requires up to 3 weeks in order to form uniform coatings; in addition to the extremely long processing time, there is a high risk of contamination during the coating step. In addition, this biomimetic coating technique usually produces a thick coating, which has a tendency to crack. In one attempt to shorten the coating time, the ionic strength of SBF was purposely increased to intensify the CaP formation rate. However, such intensification of the CaP precipitation led to less similarity of CaP to natural bone and to thicker coatings, as well as the non-desirable formation of loose particles.

As such, it would be advantageous to achieve thickness reduction for CaP implant materials, at least in part, because: (1) less material would be necessary, (2) there would be reduced residual stress, (3) better adhesion of the coating could be achieved, (4) there would be less time required to apply any coating of desired thickness, and (5) inclusion of silica ions in the form of nanocrystalline (colloidal) oxide to further enhance both bioactivity and adherence to the substrate.

It would be useful to have thin calcium phosphate coatings of about 10 μm or less can improve the bone response in orthopedic and dental implants, showing better adhesion to a variety of substrates and greater stability in the biological environment.

SUMMARY OF THE INVENTION

In one aspect, there is provided a method for preparing a biocompatible coated substrate. The method generally includes: depositing nucleation amorphous calcium phosphate sites on at least a portion of an outer surface of a substrate by: exposing at least the portion of the outer surface to a mixture having a favorable Ca/P molar ratio, and irradiating with microwave energy; and, stabilizing the deposited nucleation amorphous calcium phosphate sites on the portion of the outer surface.

In another aspect, there is provided herein a method for preparing a biocompatible coated substrate. Such method generally includes: forming amorphous calcium phosphate nucleation sites on at least a portion of an outer surface of a substrate; under microwave irradiation, and causing precipitation of CaP onto at least the portion of the outer surface in order to boost reaction between $Ca^{2+}$ and $PO_4^{3-}/HPO_4^{2-}$ ions sufficient for the $Ca^{2+}$ and $PO_4^{3-}/HPO_4^{2-}$ ions in mixture to react with the amorphous calcium phosphate nucleation sites, and to cause stabilization of the precipitated CaP.

In another aspect, there is provided herein a method for preparing a biocompatible coated substrate where the method includes: i) exposing at least a portion of an outer surface of a substrate to a mixture comprising at least calcium and phosphate ions (and in certain embodiments, silicon); and ii) exposing the mixture and substrate of step i) to microwave energy for a time sufficient to form a carbonated calcium deficient hydroxyapatite (CDHA) layer having a thickness of about 5 μm or less on at least the portion of the outer surface.

Also provided herein are substrates formed by any of the methods described herein.

In certain embodiments, wherein the layer is configured to allow for release of calcium and phosphate ions and for triggering local formation of bone-like apatite on at least portions of the outer surface wherein the Ca/P molar ratio is about 1~1.67. In certain embodiments, the mixture has a Ca/P molar ratio of at least about 1 to about 2.5.

In certain embodiments, at least a portion of the substrate comprises one or more of: a polymeric material, a metal, a ceramic, a composite, and combinations thereof.

In certain embodiments, at least the portion of the outer surface of the substrate comprises a polymeric material.

In certain embodiments, the polymeric material comprises one or more of: polycarbonates; polyurethanes; polyesters, perfluorinated hydrocarbons, acrylates, polyamides, epoxy resins, polysiloxanes and hydrogels. Non-limiting examples of polymeric materials include: polyetheretherketone (PEEK); and carbon fiber reinforced PEEK.

In certain embodiments, at least a portion of the substrate comprises a ceramics such as oxides such as alumina, zirconia, and the like; carbides such as silicon carbide, and the like; borides such as titanium boride, and the like; nitrides such as silicon nitride, titanium nitride, etc.

In certain embodiments, the substrate comprises of all of the above materials with high levels of open reticulated porosity surrounded by dense struts.

In certain embodiments, the substrate comprises one or more of: an implantable device, a dental implant, and an orthopedic implant including spinal implants. In certain embodiments, the substrate comprises one or more of: a medical device, a pacemaker, an artificial organ, heart, medical tubing such as catheters, feeding tubes, surgical drains; surgical pumps; dialysis devices.

The method any of the claims, wherein the substrate comprises a metal.

In certain embodiments, the metal is at least partially comprised of one or more of: titanium, zirconium, tantalum, niobium, gold, silver, stainless steel, tantalum, platinum, tungsten, palladium, as well as mixture, composites, combinations and/or alloys thereof.

In certain embodiments, the coating applied to the substrate has an overall thickness of about 100-900 nm to about 5-10 μm.

In certain embodiments, the coating has a thickness of about 5 μm or less.

In certain embodiments, the mixture further includes one or more of materials for facilitating bio-ingrowth between the substrate and bone or cartilage tissue; such as, but not limited to BMP, and a growth factor.

In certain embodiments, the coating layer covers a non-continuous portion of the outer surface.

In certain embodiments, the presence of nanocrystalline (colloidal) silica will enhance both bioactivity and adherence to the substrate.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

FIGS. 1A-1B: SEM (Scanning Electron Microscopy) photographs showing a biomimetic coating (Prior Art—FIG. 1A) and a microwave assisted CaP coating as now described herein (FIG. 1B).

FIG. 7: SEM photograph showing normal PEEK.

FIGS. 8A-8C: SEMs photographs showing coatings after 7 days medium incubation.

FIGS. 11A-11B: SEM photographs of 24 hrs NaOH etched PEEK surfaces are shown in FIGS. 11A (400 μm) and 11B (50 μm).

DETAILED DESCRIPTION

Figure 2A:
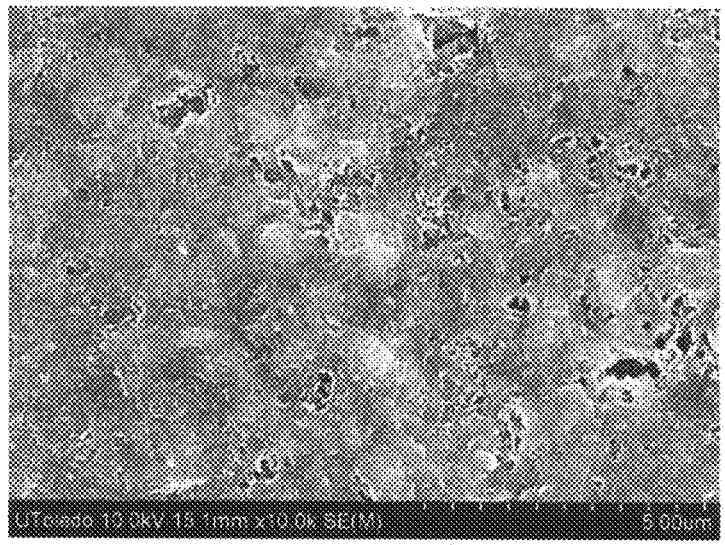
FIG. 2: SEM photograph of CaP coating on Ti6Al4V alloys (FIG. 2A) and PEEK surface (FIG. 2B).

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The presently disclosed process includes a biomimetic coating process for depositing highly bioactive calcium phosphate (CaP) coatings onto material surfaces in order to enhance the bioactivity of otherwise inert but biocompatible substrates. The deposited bone-like CaP material is highly biocompatible, bioactive, and optimally biodegradable.

In certain embodiments, the coating process described herein can include the use of a simulated body fluid (SBF), with ion concentrations, temperature, and pH almost similar to physiological conditions. Also, in certain embodiments, the chemical composition of SBF can be modified to improve the bioactivity and biocompatibility of CaP coatings or introduce specific ions into the CaP coatings.

Described herein is a long-term implant that has the desired bioactivity to form direct bonds to bone tissue. Also provided herein is a process that uses a microwave-assisted step to deposit an ultra-thin coating of a bioactive apatite material to the surface of an implant device. In a particular embodiment, the deposited material is comprised of a ceramic material similar to bone mineral belonging to the calcium phosphate (CaP) system.

The deposition process improves both the surface bioactivity and the osseointegration of implants. The ultra-thin bioactive apatite coating material can be applied to (e.g., coated on) any material surface. Non-limiting examples include: titanium, PEEK, UHWMPE, PMMA, PLA, PLGA, P3HB, alumina, zirconia and related composites, hydroxyapatite, and the like.

Furthermore, the ultra-thin bioactive apatite coating material can be applied to all types of surfaces having differing amounts of roughness (smooth vs. very rough), contours (flat vs. those containing sharp radius of curvature), as well as high porosity foams of controlled pore size distribution. It is to be noted, that in certain embodiments, the topographical features are important in the successful functioning of the implants, and the ability of the ultra-thin bioactive coating material can be applied such that the coating substantially precisely follows the surface features of the implant.

In certain embodiments, the deposited CaP coating is comprised of a carbonated calcium deficient hydroxyapatite with trace element dopants in the crystal lattice structure to mimic natural bone, making the coatings not only bioactive but optimally biodegradable. The release of calcium and phosphate ions from the coating material can trigger the local formation of bone apatite (a phase belonging to the CaP system) to the implant surface, thus intensifying the bone regeneration around the implant.

In certain embodiments, for an improved osseointegration in the subject's body, various desired surface contours of the implant can be intentionally formed on the implant. The ultra-thin coating described herein can thus keep the original desired surface contours intact.

Also, the coating thus formed is uniform and greatly resistant to cracking. Since the coatings are significantly thinner as compared to the coatings obtained via other techniques, the chances of bulk brittle failure of the ceramic coating, as well as delamination from the implant substrate is greatly diminished.

Further, in certain embodiments, the coating described herein provides a special advantage when the coating is applied to a rigid metal such as Ti. In addition, the coating also provides a special advantage to an implant when the coating is applied to a material such as a flexible polymer or, for example, when applied to PEEK.

In certain embodiments, the as-deposited coating is very thin, typically below 5 µm. Thus, being thin, the applied coating precisely adheres to the contours of the substrate and follows the surface topography.

Also described herein is a coating process which is rapid, and in certain embodiments, can take approximately half an hour (or less) to complete. In a particular embodiment, the enhanced kinetics of such coating deposition used a microwave irradiation step, as further described herein The coating process is a benign and low-temperature process that can take advantage of inexpensive raw materials. Also, the coating process is an energy saving process due to enhanced kinetics of deposition provided by microwave irradiation. Further, the process is amenable to scaling-up to an industrially viable operation.

Described herein is a method for preparing a biocompatible coated substrate comprising: i) exposing at least a portion of a substrate to a mixture comprising at least calcium and phosphate ions; and, ii) exposing the mixture and portion of the substrate of step i) to microwave energy for a time sufficient to form a carbonated calcium deficient hydroxyapatite (CDHA) layer having a thickness of about 15 µm or less on at least the portion of the outer surface.

In certain embodiments, the CDHA layer is configured to allow for release of calcium and phosphate ions, and for triggering local formation of bone-like apatite on at least portions of the outer surface.

In certain embodiments, the mixture has a Ca/P molar ratio of at least about 1 to about 2.5.

In certain embodiments, the mixture has a Ca/P molar ratio of at least about 1 to about 1.7.

In certain embodiments, the mixture includes silica.

In certain embodiments, the silica comprises nanocrystalline and/or colloidal silica.

In certain embodiments, the mixture and the portion of the substrate are exposed to microwave energy for about 1 hour or less, about 45 minutes or less, or about 30 minutes or less.

In certain embodiments, at least the portion of the substrate comprises one or more of: a polymeric material, a metal, a ceramic, a composite, and combinations thereof.

In certain embodiments, the polymeric material comprises one or more of: polycarbonates; polyurethanes; polyesters, perfluorinated hydrocarbons, acrylates, polyamides, epoxy resins, polysiloxanes and hydrogels.

In certain embodiments, the polymeric material comprises one or more of: polyetheretherketone (PEEK); and carbon fiber reinforced PEEK.

In certain embodiments, the metal is at least partially comprised of one or more of: titanium, gold, silver, stainless steel, tantalum, platinum, tungsten, palladium, chromium, cobalt, as well as alloys, mixtures, composites, combinations and/or alloys thereof.

In certain embodiments, the substrate comprises one or more of: an implantable device, a dental implant, an orthopedic implant, a medical device, a pacemaker, an artificial organ, heart, medical tubing, a catheter, a feeding tube, a surgical drain; a surgical pump; dialysis devices.

In certain embodiments, the CDHA layer has an overall thickness of about 10 µm or less.

In certain embodiments, the CDHA layer has a thickness of about 5 µm or less.

In certain embodiments, the CDHA layer substantially covers the portion of the substrate.

In certain embodiments, the CDHA layer further includes one or more biologically or pharmaceutically active compounds.

In certain embodiments, the CDHA layer further includes one or more of materials for facilitating bio-ingrowth between the substrate and bone or cartilage tissue.

In certain embodiments, the pharmaceutically active compound is a cell growth factor and/or a bone morphogenetic protein.

Also described herein is a biocompatible coated substrate made according to any one of the methods described herein.

Also described herein is a biocompatible article comprising a substrate at least partially coated with a calcium phosphate composition, the portion having been contacted with a mixture having a Ca/P molar ratio of about 1.5 to about 2.5, or a Ca/P molar ratio of about 1 to about 1.7, while exposed to microwave energy sufficient to form a layer comprised of carbonated calcium deficient In certain embodiments, the CDHA layer is bioactive and/or biodegradable upon contact with bone tissue.

In certain embodiments, the mixture comprises a simulated bodily fluid (SMF) formulation.

In certain embodiments, the mixture comprises a saline mixture having Ca2+ ions and PO43−/HPO42− ions therein.

In certain embodiments, upon implantation into bone tissue, release of calcium and phosphate ions from the CDHA layer triggers a local formation of bone-like apatite sufficient to aid bone regeneration around the article.

In certain embodiments, the article is one of: a joint implant, a spine implant and a dental implant.

In certain embodiments, the joint implant in one of: a hip, knee, elbow, ankle and shoulder implant.

In certain embodiments, the substrate includes a fiber metal porous surface.

In certain embodiments, the substrate has a textured surface.

In certain embodiments, the substrate is at least partially made from a material comprising at least one of titanium, titanium-based alloy, zirconium, niobium, cobalt-based alloy, tantalum, stainless steel and polymer.

Also described herein is a method for producing an implantable article, the method comprising: at least partially coating a portion of an implantable article with a layer comprised of carbonated calcium deficient hydroxyapatite (CDHA).

In certain embodiments, the coating step comprises subjecting at least the portion of the implantable article to a heat treatment step while at least the portion of the implantable article is exposed to a mixture having a Ca/P molar ratio in ranging from about 1 to about 2.5 for a desired period of time.

In certain embodiments, the CDHA layer is deposited at a thickness of about 15 μm, about 10 μm, about 5 μm, or below.

In certain embodiments, the portion of the implantable article is at least one of: a metal, a metal alloy, a ceramic, a natural or synthetic polymer, and composite of any of these materials.

In certain embodiments, the portion of the implantable article is at least one of: titanium, niobium, zirconium, tantalum, cobalt, alloys thereof, and stainless steel.

Also described herein is a method for the preparation of a CaP coating on an implantable article comprising the steps of: preparing a mixture having a Ca/P molar ratio in a range of about 1 to about 2.5, or in a range of about 1 to about 1.7; and applying the mixture prepared in a) onto at least a portion of an implantable article to during a heat treatment step for a sufficient time to form a layer of calcium deficient hydroxyapatite (CDHA) on the portion of the implantable article; the Ca ions in the CDHA layer being capable of forming bone-like apatite on the portion of the implantable article under physiological conditions.

In certain embodiments, the heat treatment comprises exposure to microwave energy for a period of time of about 1 hour or less, about 45 minutes or less, or about 30 minutes or less.

In certain embodiments, the mixture includes nanocrystalline and/or colloidal silica.

Also described herein is a simulated body fluid (SBF) formulation comprising:

NaCl at about 30 to about 40 g/L, $NaHCO_3$ at about 0.5 to about 2.0 g/L, KCl at about 1.0 to about 3.0 g/L, $Na_2SO_4$ at about 0.1 to about 0.2 g/L, $MgCl_2.6H_2O$ at about 0.1 to about 0.4 g/L, $CaCl_2.2H_2O$ at about 1.5 to about 2.5 g/L, $KH_2PO_4$ at about 0.5 to about 1.5 g/L, and colloidal silica (30%) at about 35 to about 45 ml.

Also described herein is a simulated body fluid (SBF) formulation comprising: NaCl at about 34 to about 37 g/L, $NaHCO_3$ at about 1.0 to about 1.2 g/L, KCl at about 1.4 to about 1.5 g/L, $Na_2SO_4$ at about 0.13 to about 0.15 g/L, $MgCl_2.6H_2O$ at about 0.2 to about 0.3 g/L, $CaCl_2.2H_2O$ at about 1.8 to about 1.9 g/L, $KH_2PO_4$ at about 0.6 to about 1.1 g/L, and colloidal silica (30%) at about 37 to about 42 ml.

In certain embodiments, the simulated body fluid (SBF) formulation comprising:

NaCl about 34.983 g/L, $NaHCO_3$ at about 1.134 g/L, KCl at about 1.4192 g/L, $Na_2SO_4$ at about 0.142 g/L, $MgCl_2.6H_2O$ at about 0.22233 g/L, $CaCl_2.2H_2O$ at about 1.8378 g/L, $KH_2PO_4$ at about 0.6805 g/L, and colloidal silica (30%) at about 40 ml.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

The value of the present invention can thus be seen by reference to the Examples herein.

Example I

The process described herein both deposits amorphous CaP (ACP) onto nucleation sites to uniformly cover a desired area of an active implant surface, and stabilizes the ACP nucleation sites to form a very thin apatite coating layer on the desired area.

In the process, the ACP nucleation sites are exposed to microwave energy. Under microwave irradiation, the formation of more ACP nucleation sites is energetically favored, as compared to formation of other CaP materials. In the microwave heating, the boiling of an aqueous environment and the precipitation of CaP boosts the reaction between $Ca^{2+}$ and $PO_4^{3-}/HPO_4^{2-}$ ions. At the end of microwave heating, the $Ca^{2+}$ and $PO_4^{3-}/HPO_4^{2-}$ ions in solution can rapidly react with ACP nucleation sites on the substrate in a phase transition process that stabilizes the deposited coating layer, with only minor changes to coating thickness.

The resulting thin CaP coatings have very desirable bioactivities without the disadvantages of coatings of a thicker variety. In certain embodiments, the coating applied to the substrate has an overall thickness of about 100-900 nm to about 5-10 μm. In further embodiments, the coating has an overall thickness of about 5 μm or less. It is to be understood that the thickness of the deposited coating can vary depending upon the length of time of deposition, which can be controlled within close limits. Accordingly, coatings of precisely defined thicknesses can be prepared according to the method of the invention.

Figure 2B:
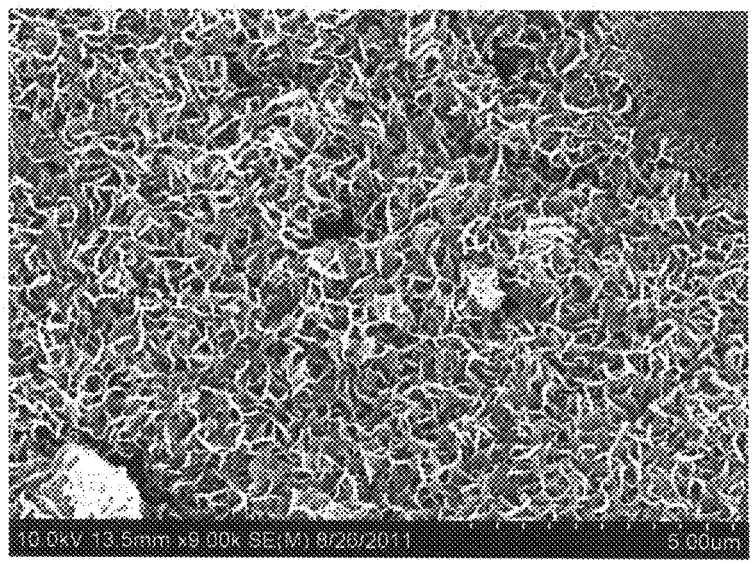

FIG. 1A (Prior Art) and FIG. 1B are SEM photographs that provide a comparison between a Prior Art biomimetic coating (FIG. 1A) and a microwave-assisted CaP coating (FIG. 1B) FIGS. 2A and 2B show microwave-assisted CaP coatings on $Ti_6Al_4V$ alloy surface (FIG. 2A) and on a PEEK surface (FIG. 2B).

Etching of Substrate

In embodiments where a substrate material may lack bioactivity, such materials can be pretreated to make their surfaces active for CaP deposition. One useful technique is etching, such as using $H_2O_2$, a strong acid, or NaOH. It is to be understood, however, that any suitable pretreatment for surface modification can be used.

Figure 3:
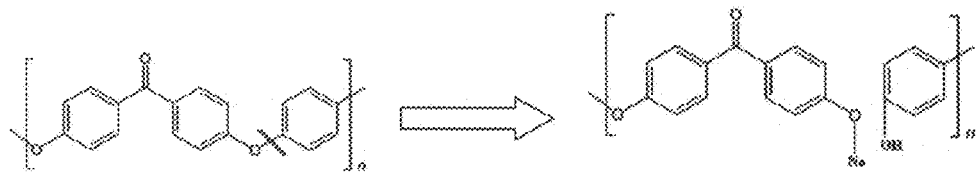
FIG. 3: Diagram showing NaOH etching to induce Na and OH groups on the surface of PEEK materials.

FIG. 3 is a chemical schematic showing a NaOH etching to induce Na and OH groups on the surface of PEEK materials. The process of applying microwave energy to accelerate the NaOH etching to the PEEK material surface thus can shorten etching time from 24 hrs to only 5 min with better results.

Figure 4:
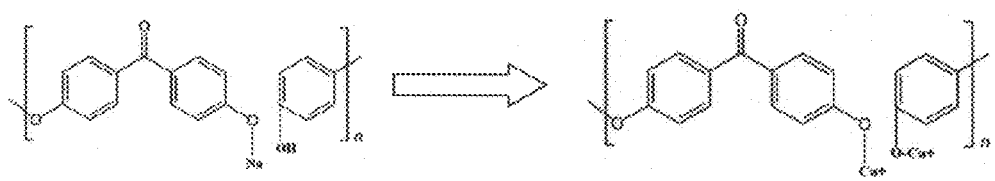
FIG. 4: Diagram showing s Na ions are replaced by Ca ions in SBF (Simulated Body Fluid) mixture and OH groups are reacted with Ca ions to from —O—Ca groups on the surface of PEEK materials, these —O—Ca groups work as nucleation sites for ions in SBF solution to form CDHA coatings on PEEK surface.

In FIG. 4, there is a chemical schematic showing that Na ions are replaced by Ca ions in SBF solution and OH groups are reacted with Ca ions to from —O—Ca groups on the surface of PEEK materials. These —O—Ca groups work as nucleation sites for ions in SBF solution to form CDHA coatings on PEEK surface.

In one embodiment, the Simulated Body fluid (SBF) shown in Table 1 was used. It is to be understood that in certain embodiments, the ranges and amounts of ingredients can be varied. The as-deposited CaP coating composition can be adjusted by adjusting the chemical composition of calcium and phosphate contained saline solution. Thus, while the SBF in Table 1 shows $K_2HPO_4$ and $CaCl_2.2H_2O$, it is to be understood that such amounts can be varied.

TABLE 1

| Order | Reagent | Example A (g/L) | Example B (g/L) | Example C (g/L) |
|---|---|---|---|---|
| 1 | NaCl | 30-40 | 34-37 | 34.983 |
| 2 | $NaHCO_3$ | 0.5-2.0 | 1.0-1.2 | 1.134 |
| 3 | KCl | 1.0-3.0 | 1.4-1.5 | 1.4192 |
| 4 | $Na_2SO_4$ | 0.1-0.2 | 0.13-0.15 | 0.142 |
| 5 | $MgCl_2 \cdot 6H_2O$ | 0.1-0.4 | 0.2-0.3 | 0.2233 |
| 6 | $CaCl_2 \cdot 2H_2O$ | 1.5-2.5 | 1.8-1.9 | 1.8378 |
| 7 | $KH_2PO_4$ | 0.5-1.5 | 0.7-1.1 | 0.6805 |

In one process, the implant substrate is placed into a calcium-and-phosphate-contained saline solution, and is heated using microwave energy. In certain embodiments, due to the water evaporation and consumption of ions in the reaction, the solution can be replenished one or more times. In such processes, for example, the implant substrate can be kept in water or ethanol to stabilize the coating being formed on the surface of the implant substrate.

The precipitated CaP coating that is formed in such microwave assisted coating process is a highly active amorphous calcium phosphate (MCP), which is especially useful as an ideal bone filler material for tissue engineering applications.

In another embodiment, materials showing bioactivity, such as bioceramics can be directly formed using the microwave-assisted process to form a CaP implant.

In Vitro Testing

Figure 5:
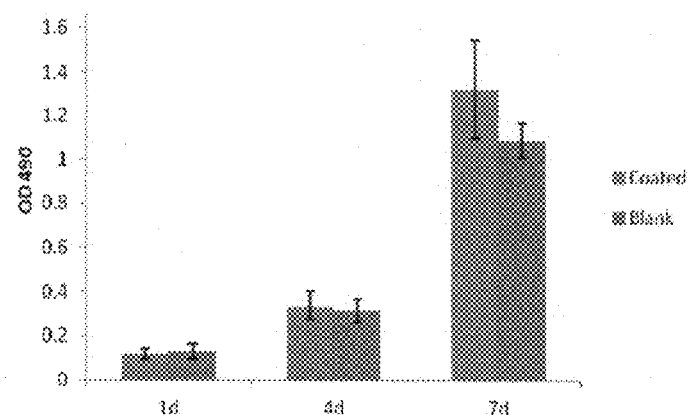
FIG. 5: Graph showing the differences between coated and blank PEEK materials.

MC3T3-E1 subclone 4 (ATCC CRL-2593) preosteoblast cells were used for in vitro testing. First, the cells were cultured at 37° C. and 5% $CO_2$ in alpha minimum essential medium (α-MEM, Thermo Scientific HyClone), augmented by 10% Fetal Bovine Serum (FBS, Thermo Scientific HyClone). The culture medium was replenished every other day until the cells reached a confluence of ~95%. Approximately 10,000 cells in 35 ml culture medium were seeded on to the sterilized sample (coated PEEK or blank PEEK) contained in the wells of 12 well plate (BD Flacon™). After 30 minutes, extra culture medium was added to wells to make the medium cover the sample surface. Total culture medium volume in each well was 1.8 ml. Cell numbers on samples were counted after 24 hours, 4 days and 7 days using CytoTox 96® Non-Radioactive Cytotoxicity Assay kit (Promega). For statistical analysis, all experiments were performed at least triplicate. FIG. 5 is a graph showing the differences between coated and blank PEEK materials.

Figure 6A:
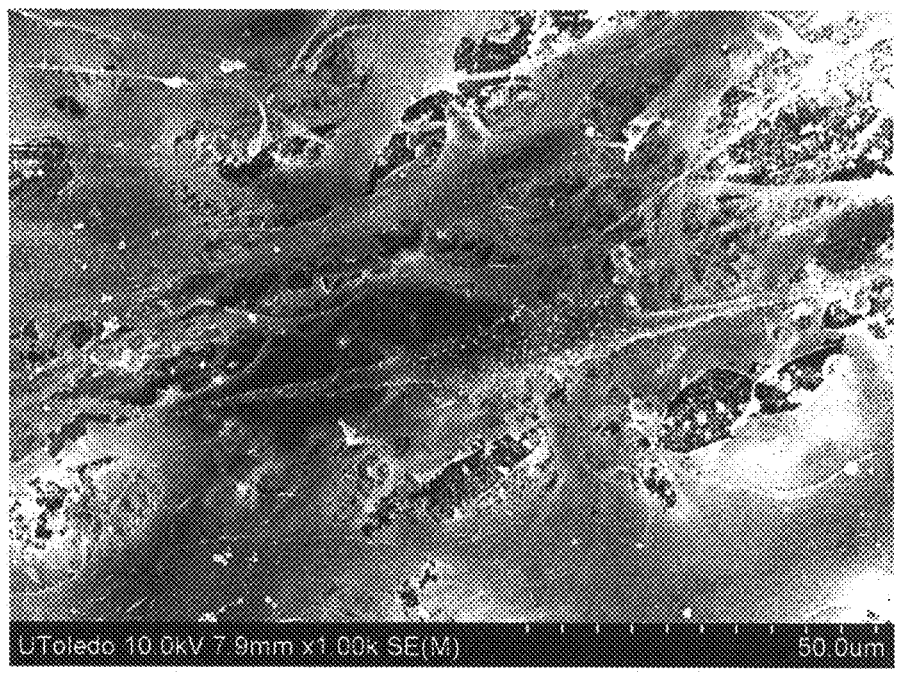
FIGS. 6A and 6B: SEM photographs showing coated PEEK material.
Figure 6B:
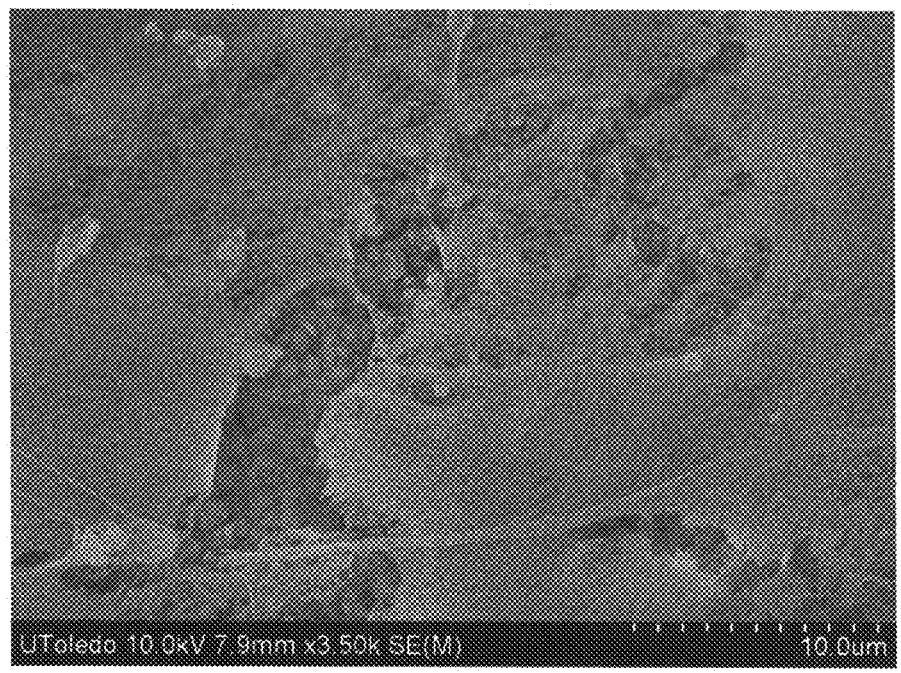

The osteoblast morphology after attachment was examined using SEM. FIG. 6A show a coated PEEK material, while FIG. 6B shows normal PEEK without any coating. In comparison, Prior Art FIG. 7 shows the surface of a normal, non-coated PEEK. It can be readily observed the MC3T3 cells on coated PEEK sample (FIG. 6A) synthesize a huge amount of collagen fibers (small fibers in SEM) with filipodia, as compared to the flat osteoblast sheet on blank PEEK surface with some cell debris (Prior Art—FIG. 7).

SEM photographs of coating on PEEK materials after 7 days medium incubation are shown in FIGS. 8A-8B. The CaP coatings are stable after 7 days complete medium incubation (FIGS. 8A-8B). In addition, it is observed after 7 days complete medium incubation, a layer of apatite deposited to the surface of CaP coating in some area, indicating the high bioactivity of such CaP coatings on PEEK surface. In contrast, observation of a blank PEEK surface cannot find such apatite deposits (Prior Art FIG. 8C).

Figure 9:
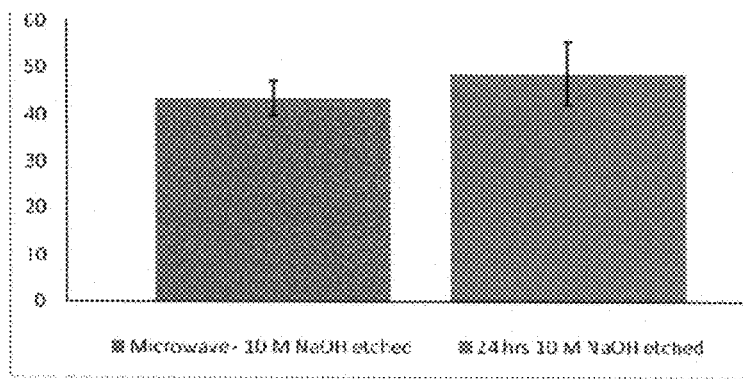
FIG. 9: Graph showing a comparison between a microwave—10M NaOH etched and 24 hrs 10M NaOH solution etched PEEK surface.

FIG. 9 is a graphs that provides a comparison of water contact angle between a microwave-assisted 10M NaOH etched PEEK material (left) and a 24 hrs 10M NaOH solution etched PEEK surface (right).

Figure 10A:
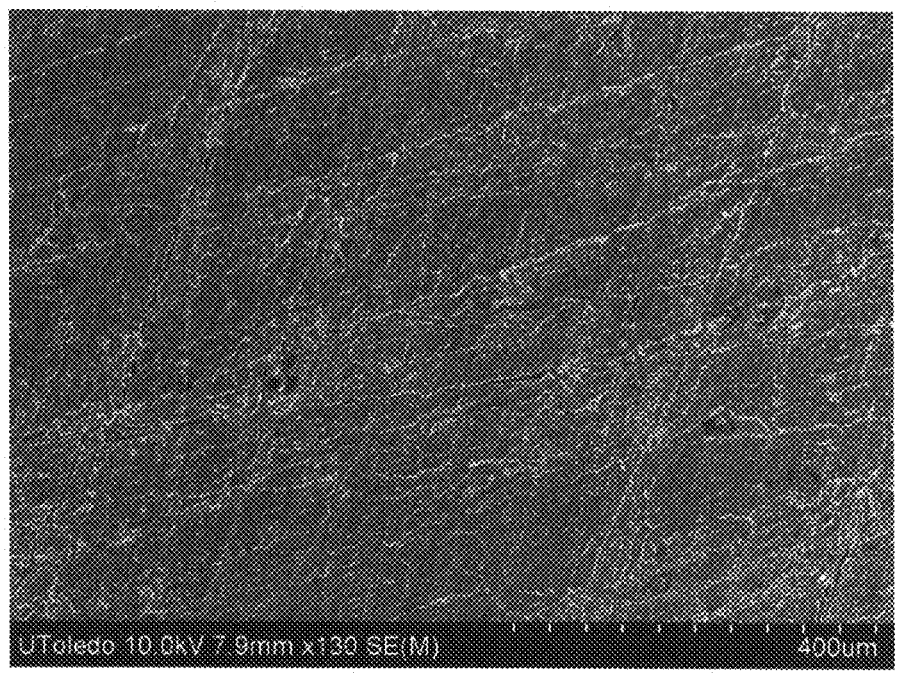
FIGS. 10A-10B: SEM photographs of a microwave—10M NaOH etched PEEK surfaces are shown in FIG. 10A (400 μm) and FIG. 10B (50 μm).

The SEM photographs in FIGS. 10A an-10B show the microwave-assisted 10M NaOH etched PEEK surfaces: FIG. 10A (400 μm) and FIG. 10B (50 μm). In comparison, see the Prior Art FIGS. 11A-11B which show SEM photographs of NaOH etched PEEK surfaces after etching for 24 hours: FIG. 11A (400 μm) and FIG. 11B (50 μm).

Figure 10B:
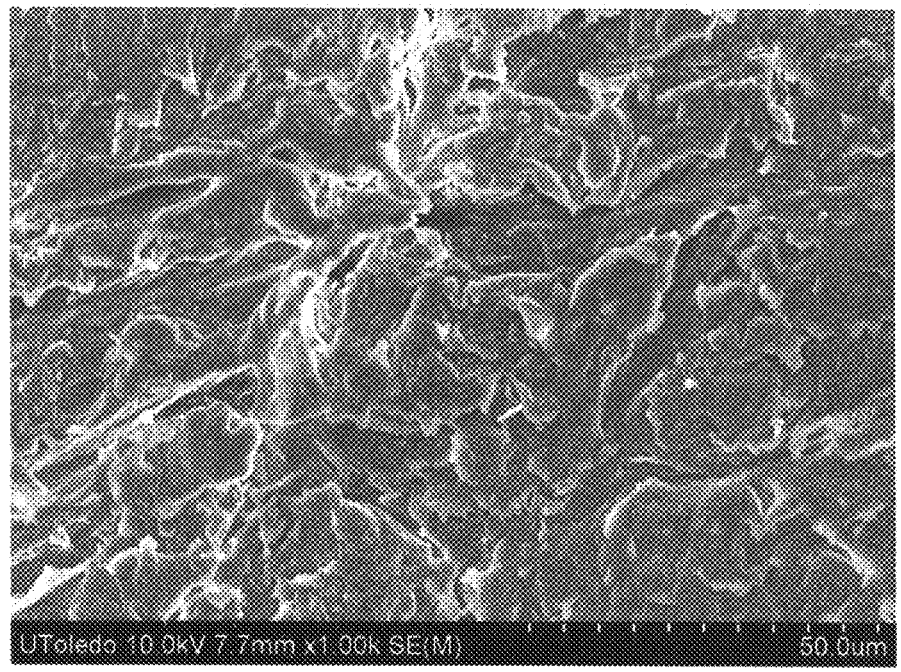

By comparing the FIGS. 10A-10B to the prior art FIGS. 11A-11B, it can readily be seen that the microwave assisted etching materials (FIGS. 10A-1B) have greatly improved surface roughness of the PEEK material, while also having a significantly shortened the etching time (from 24 hours for the prior art etched materials (FIGS. 11A-11B), to only minutes for the microwave-assisted etched materials (FIGS. 10A-10B).

Example II

The process described herein both deposits amorphous CaP (ACP) nucleation sites to uniformly cover a desired area of an active implant surface, and intensify the stabilization of the ACP nucleation sites to form a very thin apatite coating layer.

In the process the ACP nucleation sites are exposed to microwave energy. Under microwave irradiation, the formation of more ACP nucleation sites is energetically favored, as compared to formation of other CaP materials. In the microwave heating, the boiling of an aqueous environment and the precipitation of CaP boosts the reaction between nano silica, $Ca^{2+}$ and $PO_4^{3-}/HPO_4^{2-}$ ions. At the end of microwave heating, the nano silica, $Ca^{2+}$ and $PO_4^{3-}/HPO_4^{2-}$ ions in solution can rapidly react with ACP nucleation sites on the substrate in a phase transition process that stabilizes the deposited coating layer. The resulting thin CaP coatings have very desirable bioactivities without the disadvantages of coatings of a thicker variety.

Preparation is similar to Example I, followed by etching substrate and depositing coating. In one embodiment, the modified Simulated Body fluid (SBF) shown in Table 2 was used. It is to be understood that in certain embodiments, the ranges and amounts of ingredients can be varied.

TABLE 2

| Order | Reagent | Example D (g/L) | Example E (gL) | Example F (g/L) |
|---|---|---|---|---|
| 1 | NaCl | 30-40 | 34-37 | 34.983 |
| 2 | $NaHCO_3$ | 0.5-2.0 | 1.0-1.2 | 1.134 |
| 3 | KCl | 1.0-3.0 | 1.4-1.5 | 1.4192 |
| 4 | $Na_2SO_4$ | 0.1-0.2 | 0.13-0.15 | 0.142 |
| 5 | $MgCl_2 \cdot 6H_2O$ | 0.1-0.4 | 0.2-0.3 | 0.2233 |
| 7 | $CaCl_2 \cdot 2H_2O$ | 1.5-2.5 | 1.8-1.9 | 1.8378 |
| 8 | $KH_2PO_4$ | 0.5-1.5 | 0.6-1.1 | 0.6805 |
| 9 | Colloidal Silica (30%) | 35-45 ml | 37-42 ml | 40 ml |

In one process, the implant substrate is placed into a calcium-silica-phosphate-contained saline solution, and is heated using microwave energy. In certain embodiments, due to the water evaporation and consumption of ions in the reaction, the solution can be replenished one or more times.

The precipitated Si—CaP coating that is formed in such microwave assisted coating process is a highly active coating layer with intensified bioactivity due to the presence of silica, which is especially useful as an ideal bone filler material for tissue engineering applications.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated by reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A method for preparing a biocompatible coated substrate comprising:
    pretreating at least a portion of a substrate by etching the substrate with NaOH so as to activate a surface of the portion of the substrate, wherein the portion of the substrate comprises a polymeric material comprising polyetheretherketone (PEEK);
    exposing the surface to a solution mixture comprising at least calcium and phosphate ions at a Ca/P molar ratio of from about 1 to about 2.5, wherein the calcium and phosphate ions are present in the solution mixture at a concentration on the order of a millimolar concentration;
    exposing the solution mixture and the portion of the substrate to microwave energy for a time sufficient to form a calcium phosphate (CaP) layer having a thickness of about 15 μm or less on the surface, wherein the sufficient time is about 1 hour or less; and
    keeping the substrate in ethanol for a period of time to stabilize the CaP layer on the surface.

2. The method of claim 1, wherein the CaP layer is configured to allow for release of calcium and phosphate ions, and for triggering local formation of bone-like apatite on the surface.

3. The method of claim 1, wherein the mixture has a Ca/P molar ratio of at least about 1 to about 1.7.

4. The method of claim 1, wherein the solution mixture includes silica.

5. The method of claim 4, wherein the silica comprises nanocrystalline and/or colloidal silica.

6. The method of claim 1, wherein the solution mixture and the portion of the substrate are exposed to microwave energy for about 45 minutes or less, or about 30 minutes or less.

7. The method of claim 1, wherein the substrate comprises one or more of: an implantable device, a dental implant, an orthopedic implant, a medical device, a pacemaker, an artificial organ, a heart, medical tubing, a catheter, a feeding tube, a surgical drain, a surgical pump, or dialysis devices.

8. The method of claim 1, wherein the CaP layer has an overall thickness of about 10 μm or less.

9. The method of claim 1, wherein the CaP layer has a thickness of about 5 μm or less.

10. The method of claim 1, wherein the CaP layer covers the portion of the substrate.

11. The method of claim 1, wherein the CaP layer further includes one or more biologically or pharmaceutically active compounds.

12. The method of claim 11, wherein the pharmaceutically active compound is a cell growth factor and/or a bone morphogenetic protein.

13. The method of claim 1, wherein the CaP layer further includes one or more of: materials for facilitating bio-ingrowth between the substrate and bone, or cartilage tissue.

\* \* \* \* \*